United States Patent [19]

Wyrick

[11] Patent Number: 5,695,472
[45] Date of Patent: Dec. 9, 1997

[54] MODULAR AUTOMATIC OR MANUAL EMERGENCY MEDICINE INJECTION SYSTEM

[75] Inventor: Ronald E. Wyrick, Spokane, Wash.

[73] Assignee: Washington Biotech Corporation, Spokane, Wash.

[21] Appl. No.: 687,508
[22] PCT Filed: Mar. 8, 1995
[86] PCT No.: PCT/US95/02993
§ 371 Date: Jul. 30, 1996
§ 102(e) Date: Jul. 30, 1996
[87] PCT Pub. No.: WO95/31235
PCT Pub. Date: Nov. 23, 1995

Related U.S. Application Data

[63] Continuation-in-part of Ser. No. 243,641, May 16, 1994, Pat. No. 5,540,664, and a continuation of Ser. No. 262,744, Jun. 20, 1994, which is a continuation-in-part of Ser. No. 68,644, May 27, 1993, Pat. No. 5,358,489.

[51] Int. Cl.⁶ ............... A61M 5/20; A61M 5/00
[52] U.S. Cl. ............... 604/136; 604/135; 604/208; 604/211
[58] Field of Search ............... 604/134, 135, 604/136, 156, 157, 208, 211; 128/DIG. 12

[56] References Cited

U.S. PATENT DOCUMENTS

| | | |
|---|---|---|
| 2,701,566 | 2/1955 | Krug . |
| 2,750,943 | 6/1956 | Dann . |
| 3,136,313 | 6/1964 | Enstrom et al. . |
| 3,712,301 | 1/1973 | Sarnoff . |
| 3,797,489 | 3/1974 | Sarnoff . |
| 3,880,163 | 4/1975 | Ritterskamp ............... 604/136 |
| 4,073,321 | 2/1978 | Moskowitz ............... 604/208 |
| 4,085,489 | 4/1978 | Bordow . |
| 4,178,928 | 12/1979 | Tischlinger . |
| 4,214,584 | 7/1980 | Smirnov et al. . |
| 4,316,463 | 2/1982 | Schmitz et al. . |
| 4,723,937 | 2/1988 | Sarnoff et al. . |
| 4,755,169 | 7/1988 | Sarnoff et al. . |
| 4,874,385 | 10/1989 | Moran et al. . |
| 4,883,472 | 11/1989 | Michel . |
| 4,936,833 | 6/1990 | Sams . |
| 4,968,302 | 11/1990 | Schluter et al. ............... 604/135 |
| 4,973,318 | 11/1990 | Holm et al. . |
| 5,009,645 | 4/1991 | Silver et al. . |
| 5,041,088 | 8/1991 | Ritson et al. ............... 604/135 |
| 5,085,642 | 2/1992 | Sarnoff et al. . |
| 5,092,842 | 3/1992 | Bechtold et al. . |
| 5,114,406 | 5/1992 | Gabriel et al. . |
| 5,137,516 | 8/1992 | Rand et al. ............... 604/136 |
| 5,244,465 | 9/1993 | Michel . |
| 5,300,030 | 4/1994 | Crossman et al. ............... 604/136 |
| 5,358,489 | 10/1994 | Wyrick . |
| 5,425,715 | 6/1995 | Dalling et al. ............... 604/136 |
| 5,599,309 | 2/1997 | Marshall et al. ............... 604/136 |
| 5,599,315 | 2/1997 | McPhee ............... 604/135 X |
| 5,626,566 | 5/1997 | Peterson et al. ............... 604/208 |
| 5,637,094 | 6/1997 | Stewart, Jr. et al. ............... 604/135 |

FOREIGN PATENT DOCUMENTS

| | | |
|---|---|---|
| 0 577 448 | 1/1994 | European Pat. Off. . |
| 2 654 938 | 5/1991 | France . |

*Primary Examiner*—Robert A. Hafer
*Assistant Examiner*—Robert V. Racunas
*Attorney, Agent, or Firm*—Wells, St. John, Roberts, Gregory & Matkin, P.S.

[57] ABSTRACT

A modular fluid medication injection assembly (10) includes a medicant module (12) and an activator module (14). The medicant module (12) holds a replaceable, disposable syringe subassembly (24). The activator module (14) contains a driver (56) and driver release (70) for deployment and injection of the syringe subassembly. The modular design permits the use of various-sized medicant modules (12) to accommodate different sized syringe subassemblies (24) and dosages of fluid medication. Additionally, spare modules (12) may be kept on hand for administering multiple dosages from the same syringe subassembly. A carrying case (166) for the injection assembly (10) is also disclosed.

21 Claims, 5 Drawing Sheets

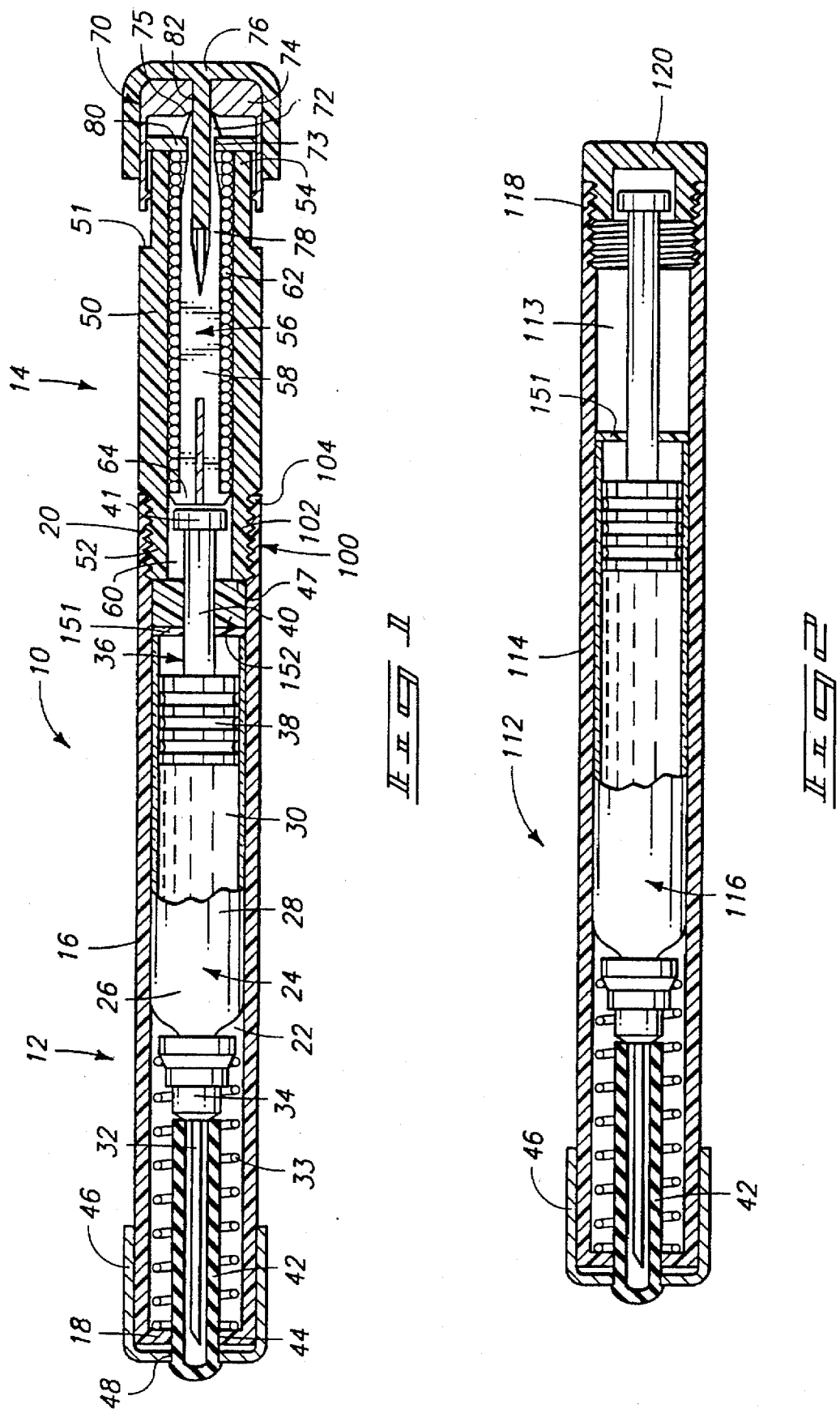

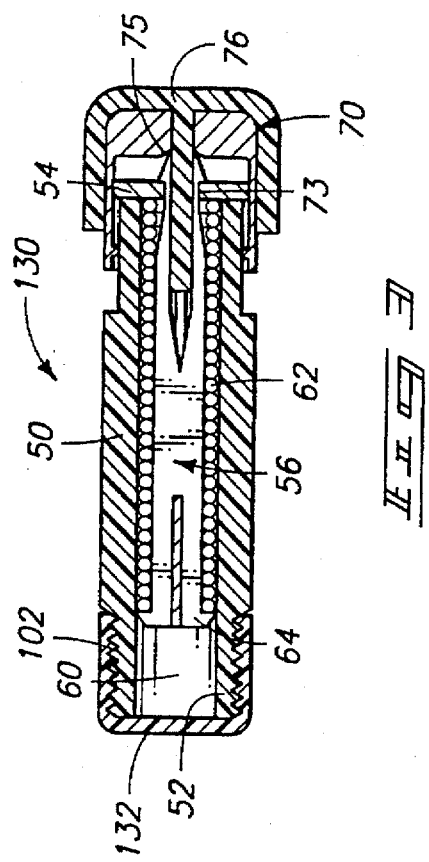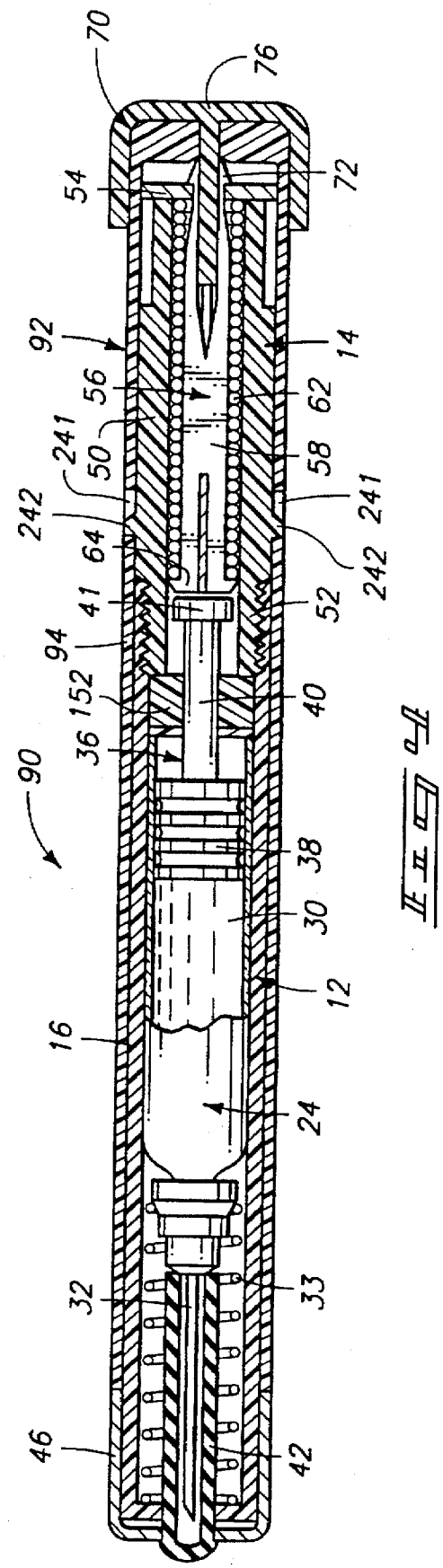

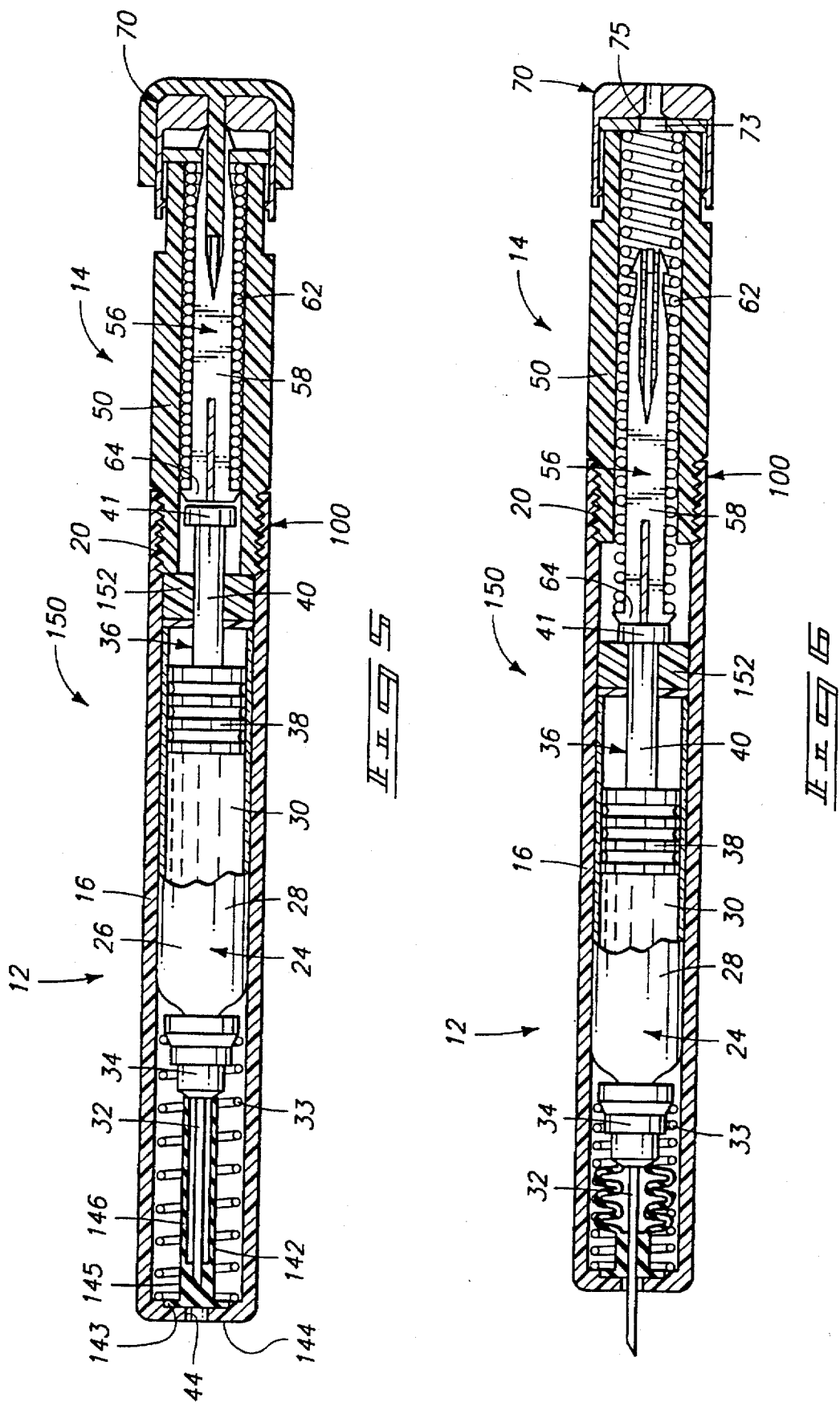

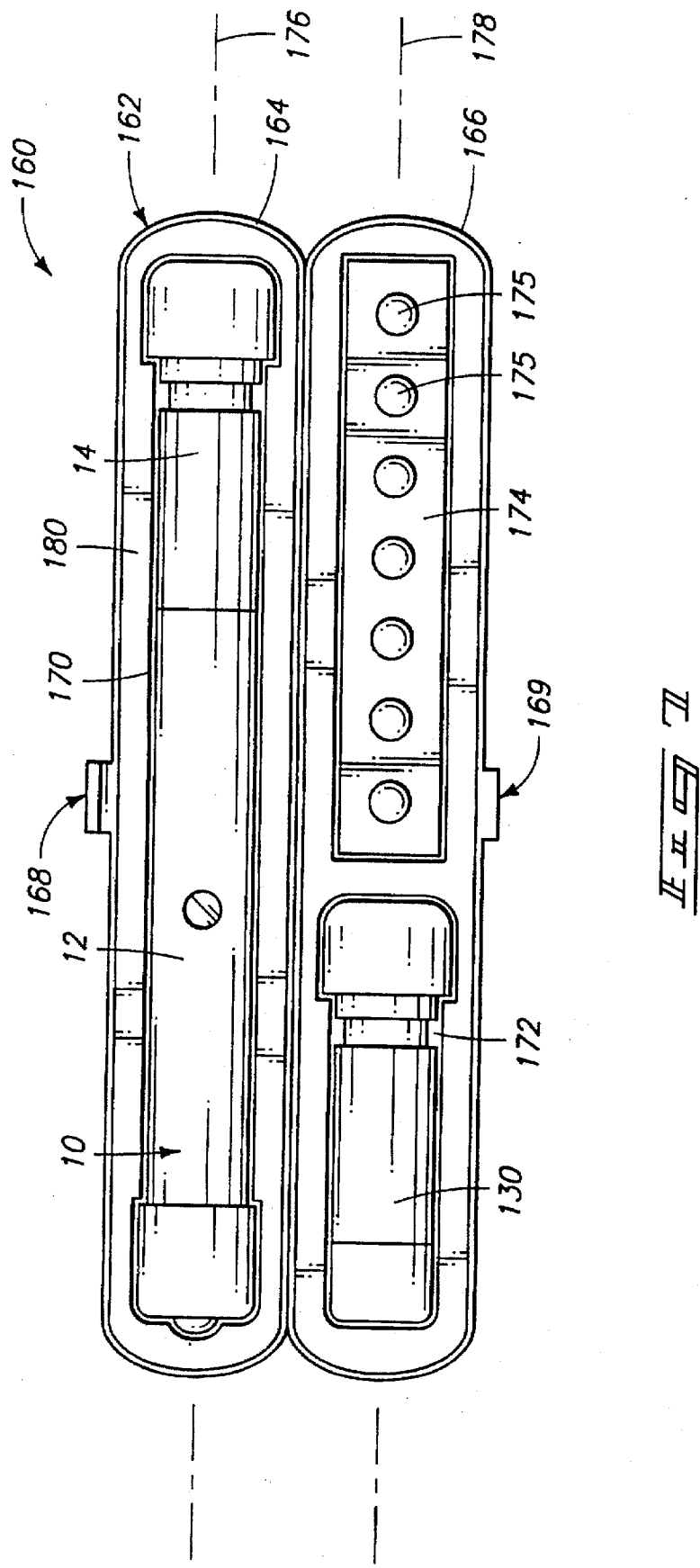

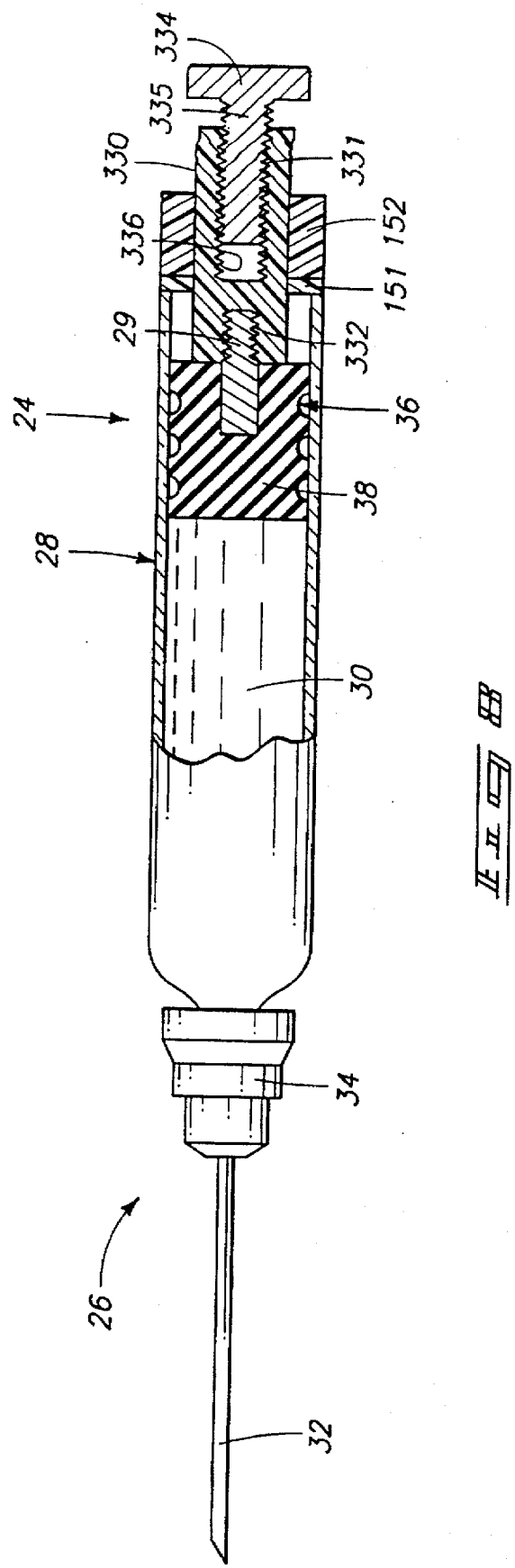

MODULAR AUTOMATIC OR MANUAL EMERGENCY MEDICINE INJECTION SYSTEM

This is a continuation of U.S. patent application Ser. No. 08/262,744, filed Jun. 20, 1994, which is a continuation-in-part of U.S. Pat. application Ser. No. 08/068,644, filed May 27, 1993 (U.S. Pat. No. 5,358,489, issued Oct. 25, 1994). This is also a continuation-in-part of U.S. Pat. application Ser. No. 08/243,641, filed May 16, 1994 (U.S. Pat. No. 5,540,664, issued Jul. 30, 1996).

TECHNICAL FIELD

This invention relates to modular automatic injection apparatuses for injecting medications into bodily tissue.

BACKGROUND ART

An automatic injection apparatus is a device which enables an individual to self-administer fluid medication by simply triggering the apparatus. The apparatus contains a measured dose of medication in a sealed sterile condition and is capable of storing the medication for an extensive period of non-use. The apparatus administers the self-contained dose automatically, so that the user does not need to visually insert the needle into his or her own tissue and then depress a plunger, such as is required in a common syringe.

Automatic injectors are particularly advantageous in emergency conditions. Such injectors can carry: antidotes for nerve gas for use during emergency chemical warfare conditions; insulin for diabetes; epinephrine for allergic reactions; or analgesics.

An automatic injector apparatus commonly includes an elongated tubular casing and a medicine "container". The medicine container contains a dose of fluid medication. Also included is a needle for injecting the medication into the user. The injector further has a trigger mechanism which causes the needle to penetrate the user's tissue and inject the medication from the container.

Typical automatic injection apparatuses have a drawback in that they administer only a single dose of medication and are not reusable. After this single use, the entire apparatus is discarded. This results in high cost and waste.

Another drawback is the relatively short storage life of some medications. The storage life of a medication is generally less than the useful life of the automatic injection apparatus. Automatic injectors are expected to be stored for long periods of time, often 3 years or more. Unfortunately, many medications do not have a comparable storage life. For example, some medications have storage lives of only approximately 1–2 years or less. Such medicines can thus become ineffective before the injector is used, resulting in the wasteful disposal of unused but fully medicated injection apparatuses. This also contributes to high costs.

The inability of automatic injection apparatus to be reloaded causes substantial addition costs in other ways. Storage of integrated one use automatic injections is made more complicated and stock must be carefully inventoried and tracked for dates of use. Medicines needing or best stored under particular conditions, such as refrigeration, are typically unavailable due to the bulk of the injection apparatus. Medicines used in automatic emergency injectors are also inventoried in addition to inventories of medications used in hospitals. These factors become particularly troublesome and costly for the military because of the logistical problems, storage considerations, and tremendous quantities involved.

Another very serious limitation is that prior automatic injectors are not capable of manual injection in instances where they fail. Prior injectors are manufactured as an integrated injection system that provides one dose of medicine. Then, the injection system is discarded. If the firing mechanism of such an injector fails, then the injection is not administered, and the user does not get to the needed medication. The internal components of such injection systems are not capable of being used manually. Thus the injectors pose a risk that due to mechanical failure medication will not be capable of administration.

Prior injectors are manufactured as a single, integrated system that provides one application of medicine, and is then discarded. However, if the trigger, firing, syringe or other mechanism fails and the injection is not administered, the user cannot access the medication contained within the sealed unitary casing. Even if the user can get at the medicine vial, the internal components are not capable of being used manually to effect an injection of the medicine. This inability to use internal components of some prior art designs results from the fact that there is either no plunger in the ampule or syringe assembly, or the plunger is a part of the driving mechanism and the syringe cannot be removed and accessed when the injector is taken apart. Thus the prior injectors pose a risk that due to mechanical failure medication will not be administered.

This invention provides an automatic modular fluid medication injection assembly in which the injection assembly can be loaded just prior to use. The injection assembly includes a medicant module which can be loaded with a variety of medications as needed for a particular situation. The medicant module can come in different sizes to accommodate different sized medicine cartridges and dosages of fluid medication. The injection assembly further includes an activator module detachably connected to the medicant module for administering the medicine from the medicant module into the bodily tissue. The assembly can be reloaded numerous times with cartridges commonly used in hospital, veterinary, or field inventories so that duplicate inventories are not required and better storage conditions are possible. As individual cartridges are used or the medicine contained therein becomes ineffective, the user simply replaces the cartridge with a new one without disposing of the injector. In this manner, only the inexpensive cartridges are replaced, and not the entire assembly. This reduces the cost significantly.

The modular construction of the novel injectors of this invention further allow easy access and removal of a syringe subassembly by the user. The activator module is quickly and easily detachable from the medicant module. This permits rapid removal of the syringe subassembly for use in applying a manual injection in the event the injector or cartridge fails, or in the event that the user simply desires to apply the injection manually. The syringe subassembly can also be replaced to refreshen the medication or exchanged for other subassemblies of different medications.

The described assembly also includes embodiments which have dual-dose capability for second dose administration either automatically injected or manually injected. The modular design has the added benefit that it permits the use of multiple ready-to-fire activator modules for rapid attachment to the medicant module to administer multiple injections of the same syringe subassembly. For instance, a first activator module can be coupled to the medicant module to administer the first dose of medication, and then a second activator module can be coupled to the medicant module to administer the second dose of medication.

BRIEF DESCRIPTION OF THE DRAWINGS

FIG. 1 is a longitudinal sectional view of a modular fluid medication injection assembly having a medicant module detachably connected to an activator module. FIG. 1 illustrates the injection assembly in a cocked position with the syringe subassembly completely within the medicant module.

FIG. 2 is a longitudinal sectional view of an alternative medicant module.

FIG. 3 is a longitudinal sectional view of a spare activator module which can be connected to a medicant module for injecting the syringe subassembly.

FIG. 4 is a longitudinal sectional view of a further novel embodiment injection assembly having a trigger handle.

FIG. 5 is a longitudinal sectional view of a modular fluid medication injection assembly according to another preferred embodiment of this invention.

FIG. 6 is a longitudinal sectional view of the injection assembly of FIG. 5 in an extended position.

FIG. 7 is a top view of an opened carrying case for storing and carrying a reloadable modular injection assembly and spare activator module according to this invention.

FIG. 8 is a side elevational view of a preferred syringe subassembly with portions shown in longitudinal sectional view.

BEST MODES FOR CARRYING OUT THE INVENTION AND DISCLOSURE OF INVENTION

FIG. 1 shows a reloadable, automatic modular fluid medication injection assembly 10 according to this invention. The modular injection assembly or "injector" has a medicant module 12 detachably connected to an activator module 14. Injection assembly 10 includes an assembly coupling 100 to alternately connect and disconnect medicant module 12 to activator module 14. Preferably, assembly coupling 100 is embodied as a threaded coupling, although other common techniques for embodying assembly coupling 100 may also be employed.

Medicant module 12 has an elongated body or barrel 16 which extends from a distal, injection, needle end 18 to a loading, coupling, or plunger end 20. Barrel 16 is a substantially cylindrical, hollow tube and is preferably formed of a hard, durable material, such as metal or plastic. Barrel 16 has a cavity 22 that is sized to house a replaceable, disposable, and manually usable syringe subassembly 24. The preferred manually usable syringe subassembly 24 is a syringe cartridge which is adapted so it can be removed from remaining portions of the injector and manually operated to effect a medicament injection.

As shown, syringe subassembly 24 has a medicament cartridge 26 which includes an ampule 28 for housing and containing a fluid medication 30. Ampule 28 is preferably a small glass or plastic vial that contains a measured amount of medication. The amount of medication (such as antidotal medicant, antibiotics, epinephrine, insulin, etc.), varies depending upon the medication and anticipated usage conditions. Cartridge 26 also has a hypodermic needle 32 mounted to the distal end of ampule 28 using a needle mounting cap 34.

Cartridge 26 further includes a fluid-tight plunger 36 for forcing the fluid medication 30 from ampule 28 through needle 32. Plunger 36 consists of a stopper 38 which sealingly engages and slides within ampule 28. Stopper 38 is preferably formed of rubber or elastomer material, and has a plunger connector, such as in the form of a mounted peg or threaded extension 29 (FIG. 8) which faces outwardly of the cartridge 26 in a longitudinal direction. The structure of cartridge 26 is commercially available or manufactured in-house by approved drug production facilities. Suitable commercially available cartridges of this construction are manufactured under the trademark TUBEX by Wyeth Laboratories, Inc., and under the trademark DOSETTE by Elkins-Sinn.

FIG. 1 also shows that plunger 36 of syringe subassembly 24 also includes a detachable plunger shaft 40 which is detachably connected to stopper 38 using a suitable plunger shaft detachable coupling. While a threaded coupling is preferred, other common techniques for providing a detachable connection between plunger shaft 40 and stopper 38 can be employed. Syringe subassembly 24 is inexpensive to manufacture and is designed to be disposed of once medication 30 has been injected into the user.

FIG. 8 shows a further preferred construction for the plunger shaft. The cartridge of FIG. 8 has an adjustable plunger shaft 330. Adjustable plunger shaft 330 is advantageously constructed using a first plunger shaft piece 331. First plunger shaft piece 331 has a first or stopper connection feature which is advantageously in the form of a threaded receptacle 332 which receives a threaded connection stud 29 mounted to the syringe stopper. The first plunger shaft piece 331 also has a second or adjustment head connection feature advantageously in the form of a threaded shaft head receptacle 336. The plunger shaft head connection receptacle 336 receives a second plunger shaft piece 335, preferably in axially adjustable relationship. The axial adjustability is most preferably accomplished using a threaded connection which allows the head 335 to be screwed into and out of the receptacle to adjust the position of the contact head 334. This construction can be used to adjust for and accommodate for variations in the length of the syringe and the position of the stopper within the ampule. Head 334 is preferably adjusted by using a gauge (not shown) which indicates the desired position of the head and then by screwing the second plunger shaft piece 335 to achieve the desired head position. Stop 152 is advantageously chosen have a length equal to approximately half the distance between stop 151 and the contacting face of the plunger head 334 where the contents of the ampule are to be dispensed in two approximately equal doses.

FIG. 1 shows that the medicant module and syringe subassembly also preferably include a removable first stop 152. Stop 152 serves to halt movement of driver 56 at an extended position after it has been released. Stop 152 is provided within medicant module 12 and positioned at least partially around plunger stem 40 of syringe subassembly 24 and within barrel 16. Stop 152 is radially sized to abut against a washer 151 which bears against the end of ampule 28. Washer 151 acts as a second stop against which the head 41 bears when first stop 152 has been removed to allow a second dose to be administered. Stop 152 has a predetermined length to provide approximately equal dosages for each injection within the same syringe subassembly. In its preferred form, removable stop collar 152 comprises first and second semi-cylindrical collar portions positioned around plunger shaft 40. Alternatively, there can be additional number of removable stops similar to stop 152 to allow to multiple doses to be administered.

Syringe subassembly 24 is sized to slide within cavity 22 of barrel 16 from plunger end 20 toward needle end 18 of medicant module 12. Syringe subassembly 24 is arranged within medicant module 12 such that needle 32 is oriented toward needle end 18 and plunger 36 is oriented toward plunger end 20. Preferably, barrel 16 has a length which entirely encloses syringe subassembly 24. Plunger end 20 of barrel 16 thus extends beyond plunger 36 of syringe subassembly 24 to protect plunger 36 during assembly of the injector.

Medicant module 12 also advantageously includes a removable protective sheath 42 provided on needle 32. Sheath 42 is preferably formed of plastic or rubber and is sized to slide over the needle to thereby protect and maintain sterility of the needle during storage. Sheath 42 has an outer diameter dimensioned to fit within needle passageway 44 formed in needle end 18 of medicant module 12.

Medicant module 12 also advantageously includes a sheath remover 46 for engaging and removing protective sheath 42 from needle 32 to expose the needle immediately prior to use. In its preferred form, sheath remover 46 has a clinching aperture 48 formed therein that is sized to slide partially onto and frictionally grasp an end portion of protective sheath 42 for removal. Sheath remover 46 is tubular shaped, and has an inner dimension which allows it to slide onto needle end 18 of barrel 16. The inner dimension is most preferably near the outer diameter of the barrel so as to provide a close frictional fit or interference fit which holds the sheath remover onto the barrel yet allows it to be detachably removed when the injection assembly is to be used.

The medicant module also preferably includes a secondary biasing spring 33. Secondary spring 33 is preferably provided within medicant module 12 between the needle end 18 and the syringe subassembly. Secondary spring 33 is used to bias syringe subassembly 24 away from needle end 18 toward the plunger end 20 of medicant module 12. This biasing action forces the syringe ampule against a shoulder 47. As shown, shoulder 47 is formed by the end surfaces of the activator module when joined with the medicant module. This serves to position the syringe subassembly within the barrel at a desired position ready for deployment.

The medicant module 12 is preferably activated by activator module 14. Activator module 14 provides controlled deployment of the syringe subassembly and automatic injection and dose administration. FIGS. 1 and 3 show a preferred activator module. As shown, activator module 14 has an elongated, tubular driver housing 50 which extends from a coupling or driver end 52 toward a trigger or proximal end 54. Driver housing 50 is a substantially cylindrical, hollow tube, and is preferably formed of a hard, durable material, such as metal or plastic. Activator module 14 includes a driver 56. Driver 56 forces syringe subassembly 24 longitudinally within barrel 16 of medicant module 12. This action injects needle 32 and discharges medication 30 from cartridge 26.

Driver 56 includes a longitudinal driver bar 58 that is slidable within driver chamber 60 of driver housing 50 between a cocked position (FIG. 1) and one or more extended positions (such as that shown in FIG. 6). Driver bar 58 is preferably a rigid piece of plastic or metal that extends axially within activator module 14. Driver 56 also has a primary drive spring 62 for forcing bar 58 toward an extended position.

Driver 56 advantageously includes an abutment or ramming head 64 which is oriented toward the driver end 52 of activator module 14. Ramming head 64 operably abuts against plunger head 41 of syringe subassembly 24 when activator module 14 is released or activated to deploy the syringe subassembly. In the assembled undeployed condition, the abutment head 64 is preferably close to or slightly spaced from the plunger head 41 without force being transferred therebetween until the activator is released. Drive bar head 64 is preferably not attached to plunger 36 of syringe subassembly 24. The unattached relationship between the driver bar and syringe plunger facilitates the connection and disconnection of the two complementary modules 12 and 16.

Ramming head 64 also advantageously forms a drive spring engagement shoulder or feature against which the drive spring bears. Drive spring 62 is axially aligned with syringe subassembly 24 and is coiled about driver bar 58. Driver 56 and ramming head 64 are entirely positioned within activator module 14 when the driver is in its cocked position.

Activator module 14 has a driver release 70 which holds driver 56 in the cocked position until the user is ready to administer the injection. Driver release 70 includes a catch 72 and a trigger 74 for releasing the catch when the trigger is depressed or otherwise activated. Driver release 70 also preferably includes a safety 76 for preventing undesired activation of the trigger and associated release of the catch.

In the FIG. 1 embodiment, trigger 74 is embodied as an end cap. This trigger end cap is longitudinally movable relative to medicant module housing 50 between a rest or extended position to a depressed position. In the depressed or activated position the trigger releases a catch 72. Depression of trigger 74 releases catch 72 which releases the activator and cause the injector to deploy the syringe and administer the dose of medication.

As shown, catch 72 consists of a detent mechanism for releasably coupling the driver to the driver release. The detent mechanism of catch 72 consists of arrow-shaped or barbed tips on multiple flexible prongs 78. Prongs 78 are advantageously formed as part of driver bar 58, or otherwise connected thereto. The prongs extend through a catch aperture 73 formed in the end wall 80 of driver housing 50. The prongs latch onto the end wall until contracted inwardly. Prongs 78 are constructed so as to allow deflection from a normal, radially expanded position into a radially constricted positions to enable the barbed tips to pass through the end wall aperture 73. If the activator is recocked, the prongs are inserted through aperture 73 where they automatically expand back to their radially expanded positions. When fully inserted through the end wall aperture, the barbed prong tips catch behind the end wall 80 and secure the driver in a cocked position.

The prongs are controllably deflected into the constricted position by a converging aperture 75 formed on the inward face of trigger 74. Trigger 74 is depressed or activated by an external force, such as depression by the user's thumb. The converging surfaces 75 engage the external sloped surfaces on the barbed tips of catch 72 as the trigger is depressed. The interaction of trigger 74 and catch 72 forces the barbed tips together until they clear end wall 80 and escape through the aperture. At this point, driver 56 is released and drive spring 62 powers the driver through activator module 14 into medicant module 12 to sequentially deploy and inject needle 32 and then discharge the medication through the injected needle.

As shown, the activator module also includes a safety 76. Safety 76 includes safety pin 82 which is inserted centrally of the multiple prongs 78. The safety pin extends through the end wall aperture between the prongs to keep them in radially expanded positions so that the barbed tips remain caught behind end wall 80. Safety pin 82 is manually removable from injector 10 when the injector is ready to be fired.

FIG. 1 further shows that injector 10 preferably includes a manually detachable assembly coupling 100. Coupling 100 is used to alternately connect and disconnect medicant module 12 to an activator, such as activator module 14. Assembly coupling 100 consists of an activator coupling part 102 provided on driver end 52 of activator module 14, and a complementary medicant coupling part 104 provided on plunger end 20 of medicant module 12. Preferably, assembly coupling 100 is embodied as a threaded coupling with complementary threads provided on activator coupling part 102 and medicant coupling part 104. Other constructions for assembly coupling 100 may also be employed.

According to this invention, modular injection assembly 10 is also designed for easy disassembly and loading. During loading, activator module 14 is disconnected from medicant module 12 to open plunger end 20 of the medicant module barrel 16. A suitable syringe assembly carrying the desired medication and dosage can then be loaded into cavity 22 through plunger end 20 in such a manner that needle 32 is oriented toward needle end 18. Once the syringe cartridge is loaded into the medicant module, activator module 14 is reconnected. The assembly is then ready for automatic deployment and discharge of cartridge 26 to administer the fluid medication.

The novel modular design constructions shown herein also facilitate manual injection, in the event that manual injection is desired or becomes necessary. In that event, the user simply disconnects activator module 14 and removes syringe subassembly 24 from the medicant module by sliding it out through the plunger end opening. The syringe subassembly can then be used in a manual fashion to inject the fluid medication.

Manual use of the syringe subassembly is important in providing fail safe injection units according to this invention. Prior art injectors were not able to be used in effecting manual injections if the need arose. This occurred because the syringe was either not capable of being used manually, or was not accessible to the user.

The modular design further has the added benefit of accommodating different sized ampules and dosages of fluid medication. FIG. 2 illustrates a medicant module 112 which is longer than medicant module 12 of FIG. 1. In most respect the medicant modules 12 and 112 are similar and similar reference numerals have been used to indicate similar parts. The lengthened medicant module 112 has an elongated barrel 114 to accommodate the longer syringe subassembly 116. Due to the modular design of this invention, where the user desires to inject a different type or dosage of medication from a larger syringe subassembly 116, the user simply attaches the larger medicant module 112 to an activator module 14 for deployment of syringe subassembly 116 and injection of the fluid medication. In this manner, the user can be equipped with an assortment of medicant modules which house various sized ampules containing multiple different types and dosages of medicines. When a type of medication is desired, the user simply selects the appropriate medicant module and attaches an activator module thereto for administration of the medication.

The medicant modules can be supplied either assembled with an activator into a ready-to-use injector, or as a separate unit for assembly with an activator module. FIG. 2 shows such a separate medicant module made in accordance with this invention. If separate, the medicant modules are preferably equipped with a removable plunger end cap or other closure, such as cap 120 in FIG. 2. Plunger end cap 120 is detachably connectable to plunger end 118 of medicant module 112 when the medicant module is disconnected from an activator module. Plunger end cap 120 serves to close barrel cavity 113, and thereby prevent syringe subassembly 116 from escaping the barrel cavity and serves to protect the syringe held therein. Plunger end cap 120 is complementarily threaded to mate with the threaded coupling on plunger end 118. When detached from medicant module 112, plunger end cap 120 serves to open barrel cavity 113 to permit removal of syringe subassembly 116 or allow coupling of the medicant module 112 to an activator module 14.

FIG. 3 shows a spare activator module 130 which includes activator module 14 of FIG. 1. Due to the modular design of this invention, additional spare, ready-to-use activator modules can be maintained in inventory. Such ready-to-use activator modules can be used to facilitate rapid multiple dose injections, such as described below in more detail. Alternatively, such modules can be used in the event that one activator module fails. Spare activator module 130 includes driver housing 50, driver 56, and driver release 70. Driver 56 is stored in its cocked position, as shown in FIG. 3. In this ready position, driver 56 is contained entirely within housing 50. The driver extends out beyond coupling end 52 only when released into an extended position. Coupling end 52 of housing 50 extends axially beyond ramming head 64. This construction better protects driver 56 when the activator module is disconnected from the medicant module.

Spare activator module 130 also includes a removable end cap 132 or other closure which is detachably connected to coupling end 52 of housing 50 when active module 130 is disassembled from a medicant module. Preferably, end cap 132 mates with threaded activator coupling part 102.

The general operation of this invention will now be described with reference to FIGS. 1-3. Individual syringe subassemblies containing different types of medication stored in various sized ampules are manufactured and can be stored separately according to their prescribed shelve lives. Alternatively, the medicant modules and activator modules can be assembled into an injector and held in a ready-to-use condition. If the medication in the syringe subassemblies exceeds the potency expiration date, the individual subassembly can be discarded. One technique for manufacturing the subassemblies is to modify existing cartridges, such as TUBEX™ and DOSETTE™ cartridges, with a plunger shaft as described herein. In this state, a user can manually administer an injection using the subassembly. This is done by injecting the needle, and manually depressing the plunger in the typical fashion.

For automatic injection, a desired subassembly of a selected medicine is loaded into an appropriately-sized medicant module 12 through plunger end 20. The subassembly is oriented therein so that needle 32 points toward needle end 18. For larger ampules, an elongated barrel 114 of medicant module 112 (FIG. 2) might be more suitable. Alternatively, the width of the ampule can be increased or decreased to adjust the desired dose volume.

Activator module 14 is then connected to medicant module 12 via threaded module coupling 100. Injection assembly 10 is now loaded, assembled, and ready for operation. To fire injector 10, sheath remover 46 is removed from needle end 18, simultaneously withdrawing sheath 42 along with it. Needle 32 is thus exposed within needle passageway 44 of needle end 18. Safety 76 is then removed, and trigger 74 is depressed to release catch 72. The energy stored in drive spring 62 is released, forcing syringe subassembly 24 through barrel 16 toward needle end 18. Needle 32 is driven out through passageway 44 to pierce the body tissue. Syringe subassembly 24 travels an effective distance to properly insert exposed needle 32 into the tissue of the user. The force provided by primary spring 62 is significantly greater than the force provided by secondary biasing spring 33 or other components. Thus biasing spring 33 contracts under the driving force. Syringe subassembly 24 halts when it reaches the end of cavity 22, with the biasing spring 33 or other components acting as a deployment stop against ampule 28 or needle cap 34.

After the syringe subassembly is deployed into an injection position, the thrusting force of driver 56 continues and depresses plunger 36. This causes cartridge stopper 38 to move and displace fluid medication 30 out through hypodermic needle 32. Plunger 36 depresses until plunger shaft head 41 abuts a stop, an end of ampule 28, or is otherwise stopped. The injector and cartridges are designed such that the distance of plunger travel is precise for an injection of prescribed dosage of medication.

After the injection is complete, the user can withdraw the injection assembly and needle. At this point, the injection assembly can be reloaded for additional application of medicine. Activator module 14 is disconnected from medicant module 12, and the spent cartridge 26 can be removed and discarded. A new syringe subassembly containing the same or different medicine can then be inserted into barrel 16. Alternatively, a different sized medicant module can be prepared with the desired ampule of medicine. Driver 56 within activator module 14 can be re-cocked using an instrument (such as a screw driver, pen, or pencil) to push bar 58 against the force of primary spring 62 until the barbed tips constrict and pass through aperture 75 in end wall 80 and then spread to lock behind the end wall. Safety 76 can be reinserted to prevent undesired firing.

Alternatively, where time is critical, the user can simply attach a ready-to-fire spare activator module, such as module 130 in FIG. 3, to the reloaded medicant module for swift activation. The use of multiple activator modules is beneficial in quick administration of multiple dosages of the same or different types of medicine. The modular design therefore offers maximum flexibility in terms of accommodating various types and dosages of medicine as well as promoting speed in emergency situations.

FIG. 4 shows an injection assembly 90 according to another preferred embodiment of this invention. Injection assembly 90 has a trigger handle 92 connected to driver release 70. The trigger handle is slidable from rest to fire positions. In the fire or release position driver release 70 fires or releases driver 56 as the trigger handle is moved to a fire position. Such motion is relative movement to the left by handle 92 as shown in FIG. 4.

Trigger handle 92 comprises a hand-fitted, circumscribing, tubular sleeve member 94 having an inner circumference diameter slightly greater than the outer circumference diameter of barrel 16 and driver housing 50. Sleeve member 94 fits over and slidably moves relative to the medicant and activator modules from its rest to fire positions. Preferably, sleeve member 94 extends from proximal end 54 of activator module 14, over driver housing 50, beyond driver end 52 of the activator module, and along medicant module 12. Preferably, sleeve member 94 extends substantially along medicant module 12 to adjacent to abut the inward face edge of sheath remover 46 when in the loaded but unfired condition. This abutting relationship serves as a safety feature in restricting longitudinal motion of the trigger sleeve in the armed condition, until the sheath remover and sheath have been removed from the muzzle end of the injector. Thus, even though the safety has been removed, the injector can in most situations only be fired after removing the sheath and sheath remover. The sheath remover thereby functions as a second safety in the constructions as shown.

FIG. 4 further shows that barrel 16 and trigger handle 92 can be constructed so as to retain the trigger handle on the barrel and provide mechanical interengagement therebetween. These functions are advantageously addressed in combination by a retainer in the form of one or more barrel retainers which engage with the trigger handle. As shown the barrel is provided with two complementary retaining dogs 242 which are received in receiving slots 241. The retaining dogs 242 are preferably provided with a lower face which is transverse in relationship to the longitudinal axis of the injector. The upper face is preferably angled to suggest a portion of a conical surface. These angled upper faces serve to facilitate assembly of the trigger handle upon the barrel by inserting the barrel into the muzzle end of the trigger handle and distorting the respective parts a sufficient amount to bring the dogs into registration with receiving slots 241.

Slots 241 are formed into or through the wall of the trigger handle. The lower faces of the dogs bear upon the lower ends of slots 241 when the injector is in the loaded and unfired position. After the safety 76 has been removed then the trigger handle 92 can be depressed to slide the trigger relative to the barrel.

The dogs 242 and slots 241 also provide mechanical interengagement between the trigger handle and barrel. More specifically, the engagement prevents excessive longitudinal motion. It further prevents relative rotational motion between the barrel and trigger handle. This anti-rotation capability allows the barrel 16 of the medicant module to be twisted relative to the barrel 50 of the activator module while holding the trigger handle. This relative twisting is needed to assemble and disassemble the modules together and apart to use or to load and unload the injector. This construction further allows the trigger handle to function more effectively in the capacities of being the manually grasped part through which force is transferred to both insert and withdraw the needle into a person being injected.

The barrel and trigger handle are most preferably constructed of transparent material, such as transparent plastic. This construction allows the user to view into the injector to determine whether there is a cartridge in the injector. It also allows the user to determine whether the medicine in the ampule has become unsuitable, such as might be indicated by discoloration or cloudiness.

To fire injector 90 the user first detaches sheath remover 46, thereby simultaneously removing sheath 42. The user then removes safety 76 to place the injector in a ready state. The user grasps trigger handle 92 in the hand and administers the medication through a swift arm stroke which drives the needle or muzzle end against the user's body at the desired point of injection. The barrel will stop upon contact with the user; but, the trigger sleeve will continue to travel, releasing driver 56. Under the force of primary spring 62, driver 56 injects needle 32 of syringe subassembly 24 into the user's tissue and dispenses a proper dosage of medication 30.

The trigger handle facilitates administration of the medication through an easy grasp-and-swing action. This is particularly useful for users who are in a weakened condition and less able to fire the more exacting "thumb" trigger described above.

FIGS. 5 and 6 show a modular injection assembly 150 according to another preferred embodiment of this invention. Assembly 150 is designed to administer multiple (typically two) injections using the same syringe subassembly. Injector 150 is very similar to injection assembly 10 of FIG. 1, and the same reference numerals are used to identify like components. Only the different features of this apparatus will be described in detail.

FIGS. 5 and 6 show an alternative protective sheath 142. Sheath 142 is advantageously made from a natural or synthetic rubber or other suitable elastomeric material. As shown, sheath 142 is constructed with a flanged head 143. Flanged head 143 is received against the muzzle or needle end wall 144 of the medicant module housing. An aperture 44 is formed in the end wall to allow the needle 32 to extend therethrough when the syringe subassembly is deployed. The protective sheath 142 has an end section 145 into which the end of needle 32 is inserted to seal and protect the sharpened needle end. The remaining tubular section 146 of sheath 142 is sufficiently flexible to allow it to buckle or collapse under the force of the primary or driver spring 62. FIG. 6 shows the syringe subassembly in an extended position.

In operation, injection assembly 150 is fired in the similar manner described above. Stop 152 halts movement of plunger 36 prior to full discharge of medication 30 from ampule 28. More particularly, plunger shoulder 41 is depressed until it engages stop collar 152. This partial travel of plunger 36 is suitable to inject a first dose of medication. If the user wishes to administer a second injection with the remaining medication, the user simply disconnects activator module 14 and partially withdraws syringe subassembly 24 from plunger end 20 of barrel 16. This allows removal of the split collar stop which is easily removed due to the split semi-cylindrical collar pieces which fit about the shaft. The syringe subassembly is reloaded into barrel 16 and spare, ready-to-fire activator module 130 is immediately connected to medicant module 12. Because spare activator module 130 is already pre-cocked, the reassembled injector is quickly ready for the second injection. With stop 152 removed, the reassembled injector assembly 150 is now ready for its second firing. When the driver is actuated, the plunger is forced farther into ampule 28 to displace the remaining fluid medication out through needle 32.

Due to the modular construction, the user can alternatively administer the second dose manually by removing the syringe subassembly from the medicant module and administering the medication using only the syringe subassembly. It should also be appreciated that the novel apparatus according to this invention can be employed to reduce or eliminate the loss of valuable medicines. Such medicines have previously been lost when used in emergency injectors. This occurs because of time deterioration and the fact that the medicine is sealed within the injector. The modular assembly of this invention can be employed in either of two ways to prevent such waste. Firstly, medicines can be installed only when needed and can be taken from regular inventories of the cartridges. Secondly, medicines used in the novel injectors can be installed and then removed in adequate time to allow the hospital or other medical services to use them in the normal course of providing services, thus preventing waste to the cartridge due to time deterioration. The modular injector is not lost merely because of medicine aging, and can continue to serve beyond the lives of the medicine.

FIG. 7 shows a carrying case 160 for porting or carrying modular fluid medication injection assemblies according to this invention. Carrying case 160 includes a rigid exterior jacket 162 configured to be alternately opened to expose an interior (as shown in FIG. 7) or closed to protect the interior. Jacket 162 is formed of two connected parts 164 and 166. The jacket is preferably formed of a hard, durable material, such as plastic. The case parts 164 can be fully detachable or connected with integrally molded plastic hinges. Metal jackets are also contemplated.

The jacket parts can be constructed to frictionally engage into a closed assembly. Alternatively, a locking clasp or latch can be provided to releasably secure the two jacket parts together. As shown, the clasp is formed of complementary components having a first clasp component 168 provided on first jacket part 164 and a second clasp component 169 provided on second jacket part 166. Clasp components 168 and 169 mate when the jacket parts are folded together to lock the parts together.

The interior of carrying case 160 can advantageously include at least three compartments: injection assembly compartment 170, spare activator compartment 172, and auxiliary compartment 174. Injection assembly compartment 170 is a recessed area formed in first jacket part 164. Injection assembly compartment 170 is elongated and sized to receive and hold modular injection assembly 10 consisting of the connected medicant module 12 and activator module 14. Injection assembly compartment 170 is aligned along a first longitudinal axis 176.

Spare activator module compartment 172 is a recessed area formed in second jacket part 166 and sized to receive and hold spare activator module 130. Auxiliary compartment 174 is also formed in second jacket part 166 and is used for storing medicinal tablets 175 or a further spare activator module 130. Spare activator module compartment 172 and auxiliary compartment 174 are aligned along a second longitudinal axis 178 that is substantially parallel to first longitudinal axis 176. According to this construction, injection assembly compartment 170 has a length substantially equal to the combined length of spare activator module compartment 172 and auxiliary compartment 174.

In an alternative embodiment (not shown) a carrying case is constructed to accommodate an injector along a first axis in a manner similar to FIG. 7. A spare medicament module as in FIG. 2 is carried along the other axis. Thus the resulting medicine injection system has a single activator and two medicant modules. Other combinations of medicant and activator modules can also be provided.

INDUSTRIAL APPLICABILITY

The invention is useful in the injection of medicines.

I claim:

1. A modular fluid medication injection system capable of automatic mechanically powered administration and manual administration of a fluid medication, comprising:

a medicant module having a needle end and a plunger end, the medicant module comprising:
a barrel having a cavity therein;
a manually usable syringe subassembly positioned within the barrel slidable within the cavity to allow deployment of the syringe subassembly, the syringe subassembly having:
an ampule for housing fluid medication;
a needle in fluid communication with said ampule;
a plunger for forcing the fluid medication from the ampule through the needle; said plunger including a plunger shaft and a plunger portion which extends from the ampule to allow manual depression of the plunger to dispense fluid from the ampule;

an activator module having a driver end detachably connected to the plunger end of the medicant module and a proximal end, the activator module comprising:

a driver for forcing the syringe subassembly through the barrel to inject the needle and displace fluid medication through the needle, the driver having a ramming head oriented toward the driver end of the activator module, the ramming head operably abutting the plunger of the syringe subassembly when the activator module is connected to the medicant module; and a driver release for controllably releasing the driver.

2. A modular fluid medication injection system according to claim 1 wherein the ramming head of the driver engages, but is not attached to, the plunger of the syringe subassembly.

3. A modular fluid medication injection system according to claim 1 wherein the barrel extends beyond the plunger at the plunger end of the medicant module to protect the plunger.

4. A modular fluid medication injection system according to claim 1 wherein the medicant module further comprises a biasing spring to force the syringe subassembly toward the plunger end of the medicant module.

5. A modular fluid medication injection system according to claim 1 further comprising a trigger handle connected to the driver release for movement from rest to fire positions, the driver release releasing the driver as the trigger handle is moved to a fire position.

6. A modular fluid medication injection system according to claim 1 wherein the activator module comprises:

a driver housing having an elongated chamber for supporting the driver therein;

a trigger handle connected to the driver release for movement from rest to fire positions, the release releasing the driver as the trigger handle is moved to a fire position; and the trigger handle comprising a circumscribing, tubular sleeve member which fits over and slidably moves relative to the driver housing; the sleeve member extending from the proximal end of the activator module, over the driver housing, beyond the driver end of the activator module, and at least partially along the medicant module.

7. A modular fluid medication injection system according to claim 1 wherein the medicant module further comprises a removable protective sheath provided on the needle.

8. A modular fluid medication injection system according to claim 1 wherein the medicant module further comprises:

a removable protective sheath provided on the needle; and a sheath remover for engaging and removing the protective sheath from the needle to expose the needle.

9. A modular fluid medication injection system according to claim 1 wherein the medicant module further comprises:

a removable protective sheath provided on the needle; and a sheath remover for engaging and removing the protective sheath from the needle to expose the needle, the sheath remover having an aperture formed therein that is sized to slide partially onto and frictionally grasp the protective sheath for removal.

10. A modular fluid medication injection system according to claim 1 further comprising:

an assembly coupling to alternately connect and disconnect the medicant module to the activator module, the assembly coupling comprising an activator coupling part provided on the driver end of the activator module and a complimentary medicant coupling part provided on the plunger end of the medicant module.

11. A modular fluid medication injection system according to claim 1 wherein the activator module and the medicant module are detachably connected using a threaded coupling.

12. A modular fluid medication injection system according to claim 1 wherein the medicant module further comprises a removable plunger end cap detachably connectable to the plunger end of the medicant module when the medicant module is disconnected from the activator module, the plunger end cap serving to close the barrel cavity and thereby prevent the syringe subassembly from escaping the barrel cavity when attached to the medicant module and serving to open the barrel cavity and allow removal of the syringe subassembly when detached from the medicant module.

13. A modular fluid medication injection system according to claim 1 wherein the activator module further comprises:

a driver housing having an elongated chamber for supporting the driver therein; and a removable driver end cap detachably connectable to the driver housing at the driver end of the activator module when the activator module is disconnected from the medicant module.

14. A modular fluid medication injection system according to claim 1 further comprising a removable stop within the medicant module for halting movement of the driver at an extended position.

15. A modular fluid medication injection system according to claim 1 further comprising a removable stop within the medicant module for halting movement of the driver at an extended position, the removable stop being positioned at least partially around the plunger of the syringe subassembly to prevent full discharge movement of the plunger.

16. A medicant module for use in a fluid medication injection system, the medicant module comprising:

a barrel having a cavity therein;

a manually usable syringe subassembly positioned within the barrel slidable within the cavity to allow powered mechanical deployment of the syringe subassembly, the syringe subassembly having:

an ampule for housing fluid medication;

a needle in fluid communication with said ampule;

a plunger for forcing the fluid medication from the ampule through the needle; said plunger including a plunger shaft and a plunger portion which extends from the ampule to allow manual depression of the plunger to dispense fluid from the ampule;

a removable plunger end cap detachably connectable to the plunger end of the medicant module, the plunger end cap serving to close the barrel cavity and thereby prevent the syringe subassembly from escaping the barrel cavity when attached to the medicant module and serving to open the barrel cavity and allow removal of the syringe subassembly when detached from the medicant module.

17. A modular fluid medication injection system according to claim 16 wherein the barrel extends beyond the plunger at the plunger end of the medicant module to protect the plunger.

18. A modular fluid medication injection system according to claim 16 wherein the medicant module further comprises a biasing spring to force the syringe subassembly toward the plunger end of the medicant module.

19. A modular fluid medication injection system according to claim 16 wherein the medicant module further comprises a removable protective sheath provided on the needle.

20. A modular fluid medication injection system according to claim 16 wherein the medicant module further comprises:

a removable protective sheath provided on the needle; and a sheath remover for engaging and removing the protective sheath from the needle to expose the needle.

21. A modular fluid medication injection system according to claim 16 wherein the medicant module further comprises:

a removable protective sheath provided on the needle; and a sheath remover for engaging and removing the protective sheath from the needle to expose the needle, the sheath remover having an aperture formed therein that is sized to slide partially onto and frictionally grasp the protective sheath for removal.

* * * * *